(12) United States Patent
Takahashi (10) Patent No.: US 7,214,059 B2
(45) Date of Patent: May 8, 2007

(54) BONE COLLECTING DEVICE (76) Inventor: Atsushi Takahashi, 20-15-1, Kizaki, Tsuruga, Fukui 914-0814 (JP)

( * ) Notice: Subject to any disclaimer, the term of this patent is extended or adjusted under 35 U.S.C. 154(b) by 377 days.

(21) Appl. No.: 10/469,831

(22) PCT Filed: Mar. 5, 2002

(86) PCT No.: PCT/JP02/01991

§ 371 (c)(1), (2), (4) Date: Jan. 16, 2004

(87) PCT Pub. No.: WO02/069838

PCT Pub. Date: Sep. 12, 2002

(65) Prior Publication Data

US 2004/0115590 A1   Jun. 17, 2004

(30) Foreign Application Priority Data

Mar. 6, 2001   (JP) ............................. 2001-061601

(51) Int. Cl.
  *A61C 17/14* (2006.01)
(52) U.S. Cl. ......................................... 433/92; 433/91
(58) Field of Classification Search ................. 433/92; 210/406–409; 604/313, 315, 318–319
  See application file for complete search history.

(56) References Cited

U.S. PATENT DOCUMENTS

| | | | |
|---|---|---|---|
| 1,664,369 A * | 3/1928 | Mauer ........................ 433/88 |
| 3,890,712 A * | 6/1975 | Lopez ......................... 433/92 |
| 4,083,706 A * | 4/1978 | Wiley ........................ 55/385.1 |
| 4,468,217 A * | 8/1984 | Kuzmick et al. ............... 604/48 |
| 4,813,931 A * | 3/1989 | Hauze ........................ 604/540 |
| 4,886,492 A * | 12/1989 | Brooke ....................... 604/541 |
| 4,957,492 A * | 9/1990 | McVay ........................ 604/319 |
| 5,015,243 A * | 5/1991 | Schifano ..................... 604/315 |
| 5,149,325 A * | 9/1992 | Telang et al. ................ 604/119 |
| 5,158,533 A * | 10/1992 | Strauss et al. .............. 604/6.09 |
| 5,279,599 A * | 1/1994 | Wilk .......................... 604/317 |
| 5,630,939 A * | 5/1997 | Bulard et al. ............... 210/416.1 |
| 5,713,879 A * | 2/1998 | Schneider .................... 604/319 |
| 5,766,134 A * | 6/1998 | Lisak et al. ................. 600/562 |
| 5,779,649 A * | 7/1998 | Herbert ....................... 600/571 |
| 5,807,353 A * | 9/1998 | Schmitz ....................... 604/264 |
| 5,941,873 A * | 8/1999 | Korenfeld .................... 606/1 |
| 6,135,770 A * | 10/2000 | Bembenek et al. .............. 433/88 |
| 6,183,254 B1 * | 2/2001 | Cohen ......................... 433/92 |
| 6,299,444 B1 * | 10/2001 | Cohen ......................... 433/91 |
| 6,440,109 B1 * | 8/2002 | Mastel ........................ 604/313 |
| 6,942,650 B1 * | 9/2005 | Schultz et al. ............... 604/315 |

\* cited by examiner

*Primary Examiner*—Cris Rodriguez
*Assistant Examiner*—Patrick Kilkenny
(74) *Attorney, Agent, or Firm*—Quintero Law Office (57) ABSTRACT

A bone piece collecting device, wherein, when bone pieces are mixing agitated with the other substances while preventing the loss of the cut bone pieces collected on a filter and contamination thereof by saliva by a self-bone transplanting method, a filter part is installed in a filter holder with impermeability to eliminate the operation for transferring the bone pieces to the other container, a collected bone container for filling bones is prevented from being fallen down by stably fixing the container to a cuff for operation or an operation table with an adhesive tape or a magic tape installed at the bottom part of the filter holder so as to facilitate the removal of the collected bones, and a gradient is marked on the transparent or semi-transparent material of the filter holder so that the amount of collected bones can be weighed easily.

5 Claims, 8 Drawing Sheets

BONE COLLECTING DEVICE

BACKGROUND OF THE INVENTION

1. Field of the Invention

The invention relates to a technology for collecting bone pieces when an implant socket is drilled during a dental implant operation or a technology for selectively collecting a bone from a non-transplant site by a bone piece collecting device and filling collected bone pieces to a transplant site.

2. Description of the Related Art

In a conventional implant operation, a self-bone transplanting method is often applied when the amount of the bone is insufficient to be transplanted into a transplant site. When an implanted socket is drilled in a jawbone, cut bone pieces from the jawbone, and blood, saliva, cooling water from a turbine are filtered and selectively collected by a sucking chip of a dental vacuum device via a filter. The collected bone piece itself can be directly transplanted by a syringe-shaped bone piece collecting device. Alternatively, the collected bone piece can be transplanted after it is transferred to a dappen dish and is mixingly agitated with the other substances. However, in clinical application, in view of easy application, osteoconduction, or infection control, the problem generated from the self-bone may increase after the collected bone is transferred to the other container and mixing agitated with the other substances. As stated above, during the normal transplantation, the cut bone pieces from the jawbone, used as bone filling material, is selectively collected by a sucking chip of the dental vacuum device through the filter when the amount of the bones is insufficient to be transplanted such that the self-bone transplanting method is used. The collected bone piece is mixingly agitated with the other substances. Furthermore, when collecting the cut bone pieces without loss, blood or saliva other than normal saline may also be collected when bone pieces lost in the oral cavity are suctioned. Thus, the collected bone may be contaminated.

To solve the above problem, the purpose of the invention is to enable the collected bone pieces to be mixingly agitated with the other substances without transferring to the dappen dish or other containers such that the bone filling operation can be simplified. In addition, the collecting bone container for filling the bone is prevented from being fallen down such that the collected bone can be collected without loss. Furthermore, the collected bone can be removed easily, and the amount of the collected bone and that of the substances mixingly agitated with the collected bone can be weighed easily. Thus, the collected bone pieces can be prevented from loss and from contamination by saliva.

SUMMARY OF THE INVENTION

To attain the above the object, the invention provides a bone piece collecting device for filtering and collecting bone piece from an oral cavity. The device includes a suction duct, a main unit body, a filter member, and a filter holder with impermeability. The suction duct extracts liquid from the oral cavity, including at least bone piece, saliva, and blood. The main unit body includes a suctioning side part and a base end side part connected to the suctioning side part via an intermediate portion, and is coaxially connected to the suction duct. The base end side part, through which the liquid excluding the bone piece passes, is detachable from the suction duct. The suctioning side part, through which the liquid including at least the bone piece passes, is detachable from the base end side part. The filter member includes a filter part, a first joint part and a second joint part. The filter member filters the bone piece and joints the base end side part and the suctioning side part, and is detachably disposed at the intermediate portion in the main unit body. The filter part is container-shaped, and filters the bone piece from the liquid. The first joint part is fitted to an inner side of an opening of the base end side part. The second joint part is fitted to the suctioning side part and located around the first joint part, and protrudes from the opening of the base end side part. The filter holder is fitted to an outer wall of a mesh of the filter member removed from the main unit body after collecting the bone piece. The area of the bottom part of the filter holder exceeds that of the filter member such that the filter member can be stably positioned. After bone piece in the filter member press fitted to the filter holder is mixingly agitated with the other substances, it is removed. To improve application ability, osteoconduction, and infection control, when the self-bone is mixingly agitated with the other substance, the bone pieces are selectively collected by the filter assembled on the sucking chip of the dental vacuum device. When the collected bone pieces are mixingly agitated with the other substances, including liquid, held in the filter holder, its application ability can be improved and the amount of the collected bone pieces can be prevented from reducing since it needs not to be transferred to the dappen dish.

In a preferred embodiment, the device further includes an adhesive tape or a magic tape attached at the is bottom part of the filter holder. Thus, when the filter holder is fixed to an operation cuff or an operating table via the adhesive tape or magic tape, the bone filling material, including the bone pieces, can be removed without the need to manually hold the filter holder. Since the bone piece collecting device including the filter holder is prevented from tipping over or being fallen down, the precious collected bone pieces can be prevented from dispersing and that it facilitates the removal of the collected bone.

In another preferred embodiment, the filter holder is transparent or semi-transparent with a gradient on its inner wall and its outer wall such that a volume received in the filter holder can be easily weighed. Thus, it becomes possible to easily grasp in proportion the optimum amount of collected bone pieces and with the other substances mixingly agitated with the bone pieces.

In another preferred embodiment, the main unit body further includes a flexible bone collecting dam that includes a first dam joint portion, a second dam joint portion, and at least one spike. The first dam joint portion is annular, and includes an opening at an inner side. The first dam joint portion surrounds a bone cutter, and is shaped as a hollow tube and made of flexible resin or made by pressing simulating annealing wire into insert-shaped flexible resin so as to be deformable. Thus, the first dam joint portion can be adapted to a site for operation. The second dam joint portion passes through an inner side of a hollow tube for is jointing the suctioning side part, and is cylindrical. The spike is disposed on a bottom of the first dam joint portion, and fixes the flexible bone collecting dam to an incision site. Thus, the first dam joint portion is closely adjacent to the bone, and is disposed around a site that the bone is cut. By such sucking, the saliva can be prevented from sucking so that a maximum amount of collected bone can be collected without losing the collected bone.

BRIEF DESCRIPTION OF THE DRAWINGS

The present invention can be more fully understood by reading the subsequent detailed description and examples with references made to the accompanying drawings, wherein.

DETAILED DESCRIPTION OF THE INVENTION

Referring to figures, an embodiment of the invention is described in the following.

FIGS. 1–12 show an embodiment of the invention. In figures, the, same reference in different figures represents the same component.

Figure 5:
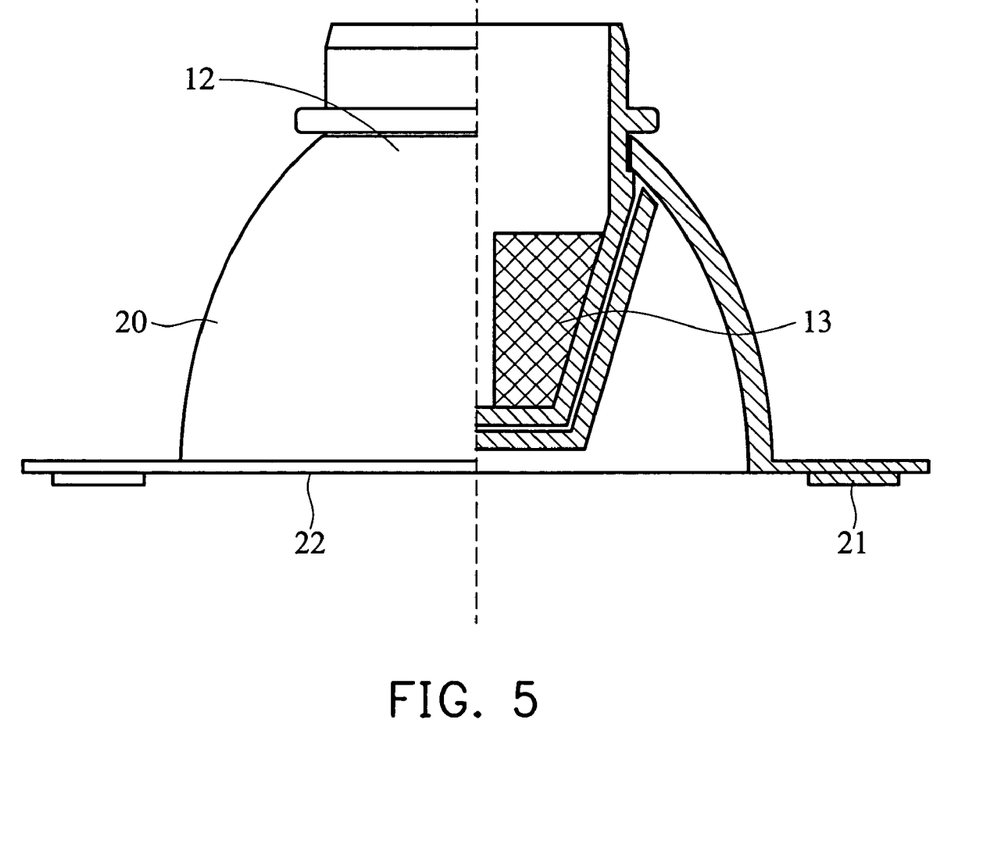
FIG. 5 is a side view of the filter member held by a filter holder.
Figure 6:
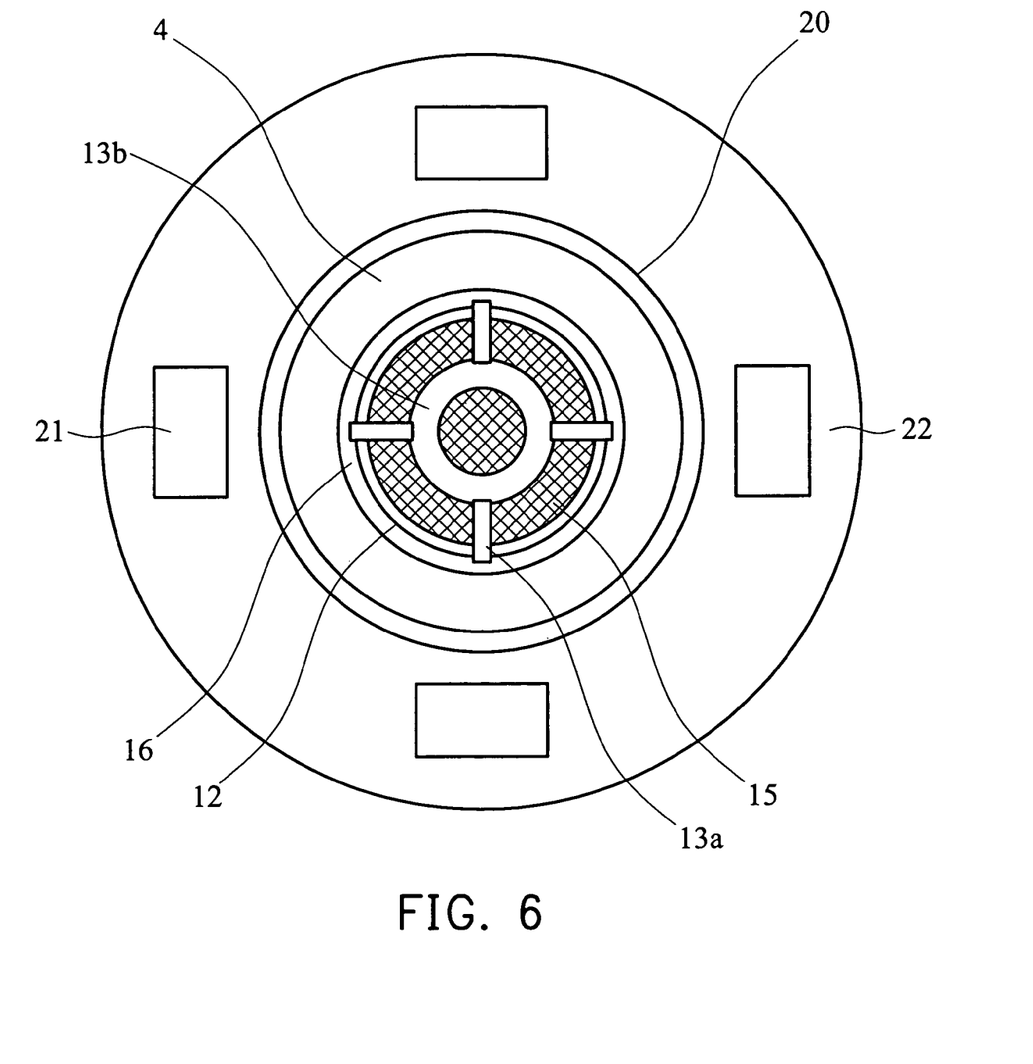
FIG. 6 is a schematic view showing an inner part of the filter holder holding the filter member.

Although the basic structure of the invention is similar to conventional devices, the characteristics of the invention are shown in FIGS. 5–6. Specifically, in FIGS. 5–6, a filter member 4 for collecting bone pieces is assembled on a filter holder 20. Also, in FIGS. 7–8, a flexible bone collecting dam 30 is disposed at a front end portion 5 of a suctioning side part 2.

Figure 1:
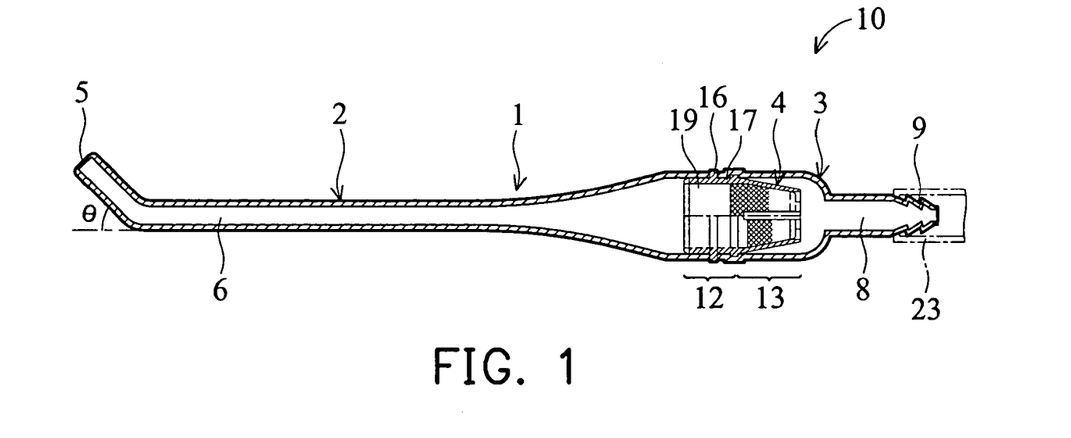
FIG. 1 is a cross section of a bone piece collecting device as disclosed in the invention.
Figure 2:
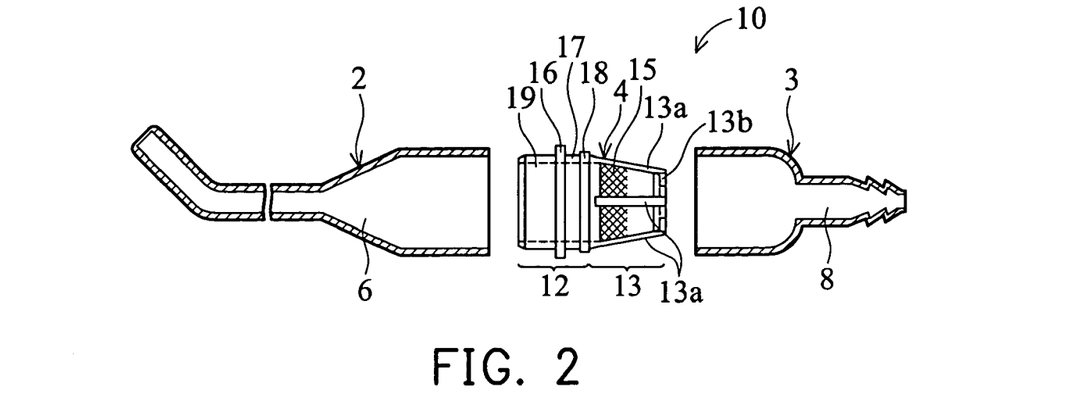
FIG. 2 is an exploded enlarged view of FIG. 1.
Figure 3:
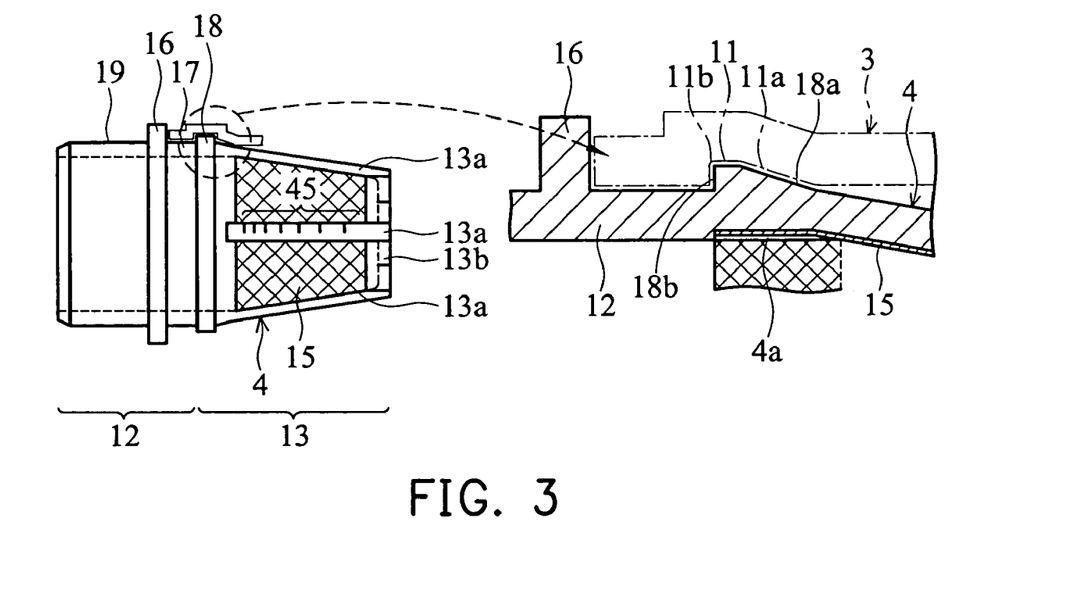
FIG. 3 is an enlarged view of a filter member in FIG. 1, wherein a portion, engaged with a base end side part in FIG. 1, of the filter member is shown in an enlarged manner.
Figure 4:
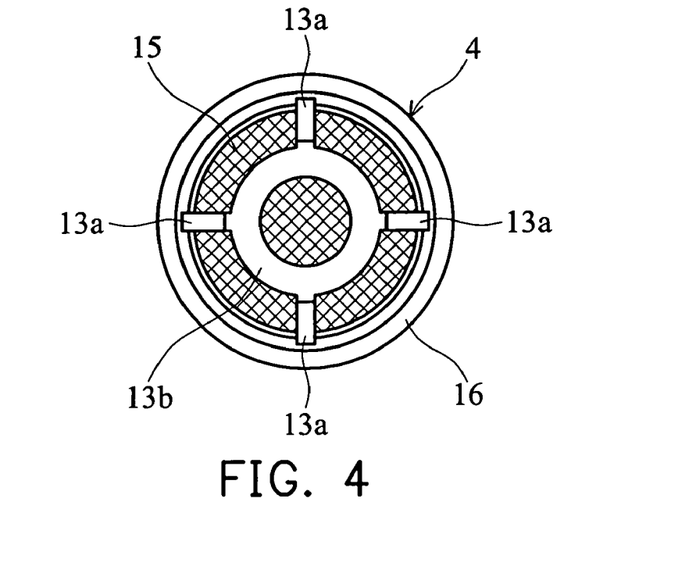
FIG. 4 is a bottom view of the filter member.
Figure 7:
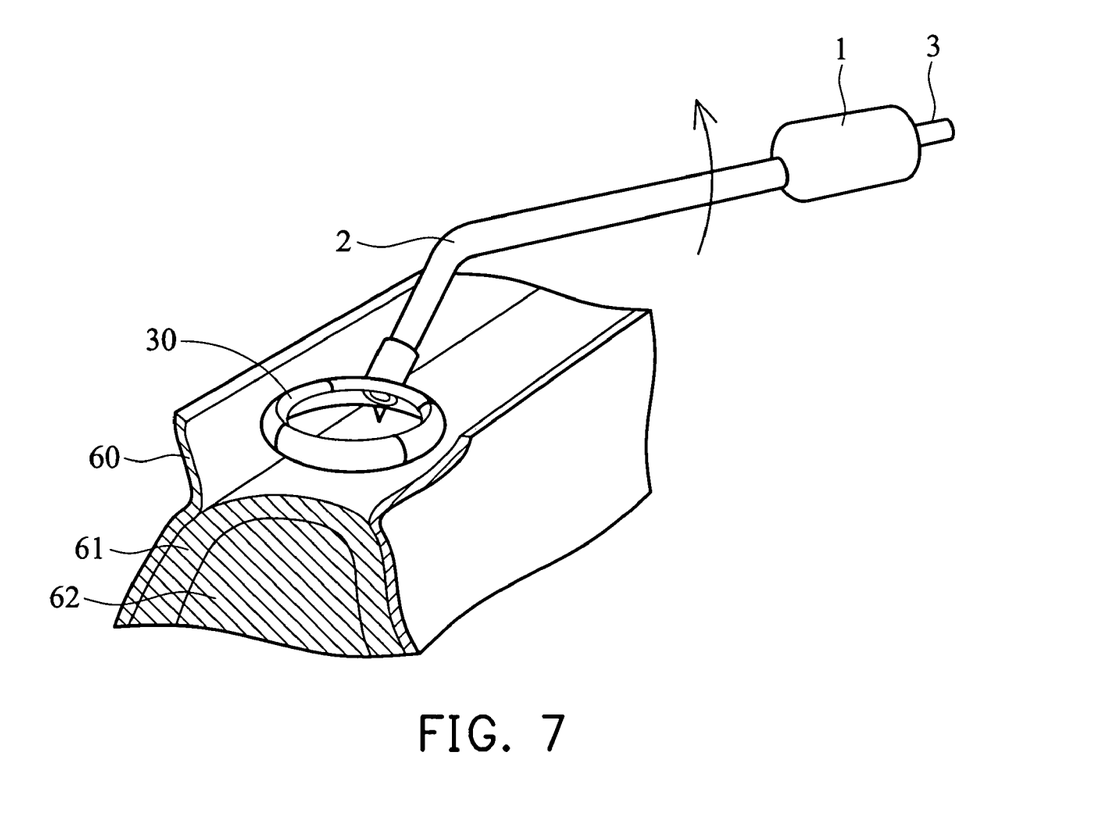
FIG. 7 is a schematic view showing a main unit body, including a flexible collecting bone dam, disposed on the alveolar bone.
Figure 8:
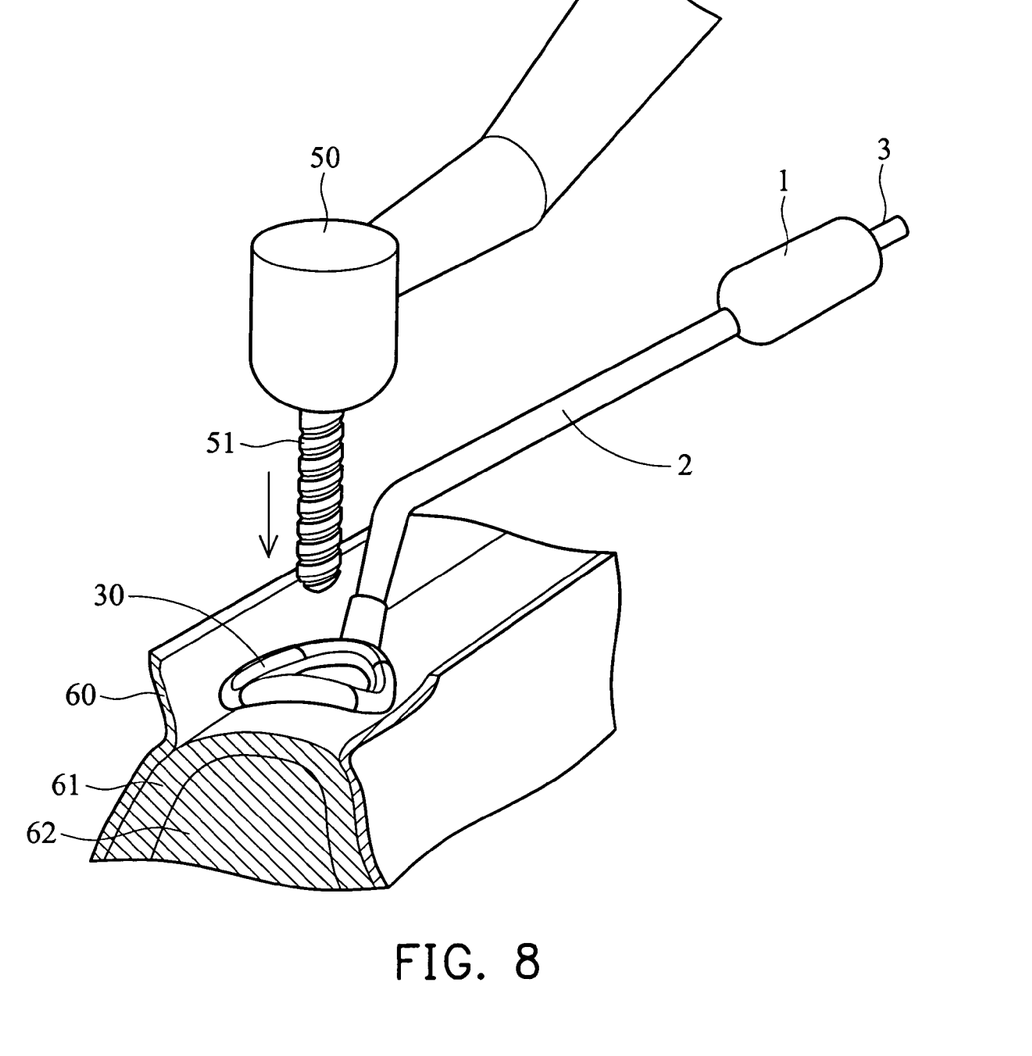
FIG. 8 is a schematic view showing that the main unit body is disposed on the alveolar bone by a spike, wherein the flexible collecting bone dam corresponds to the alveolar bone.
Figure 9:
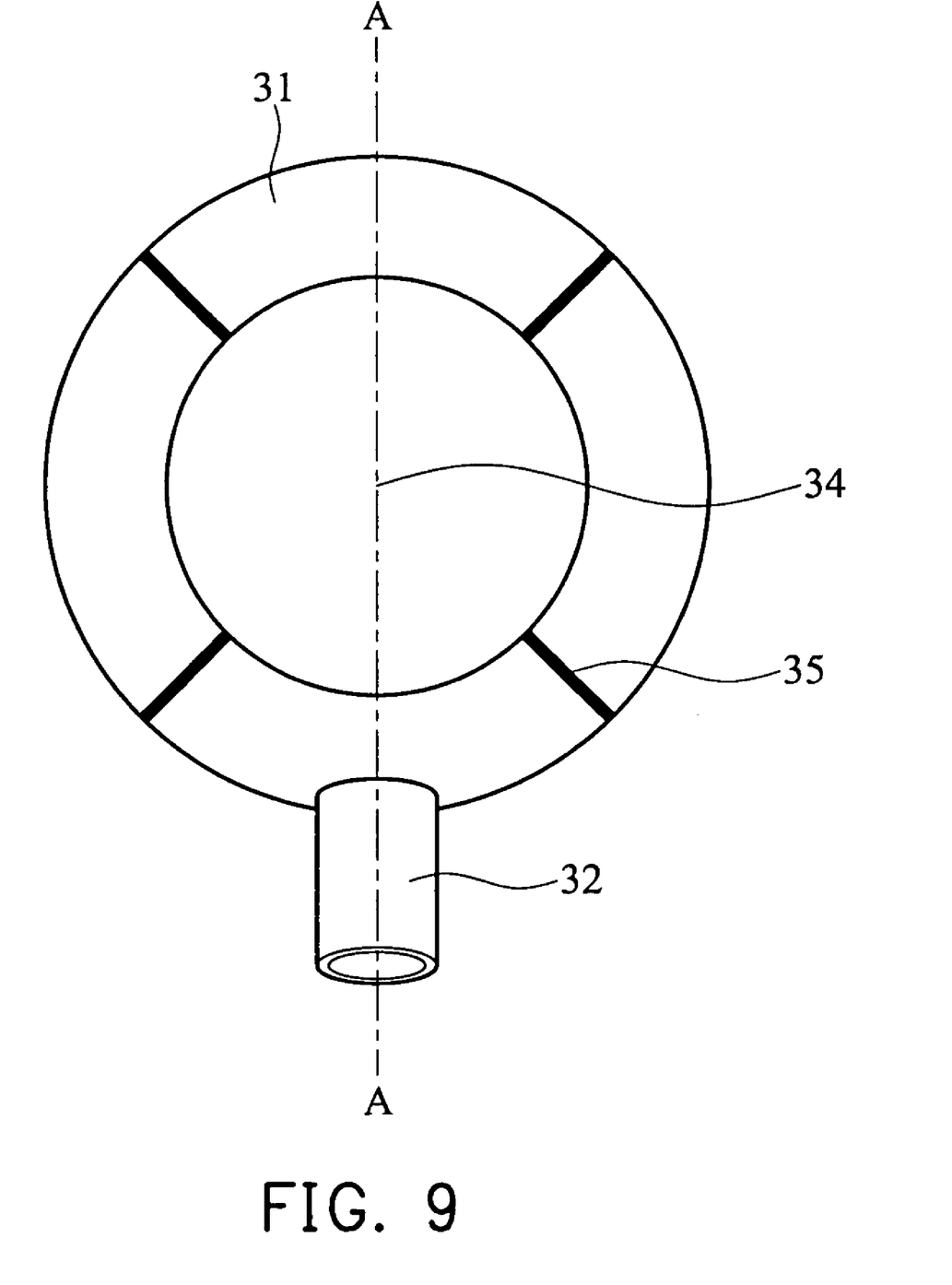
FIG. 9 is a top view of the flexible collecting bone dam.
Figure 10:
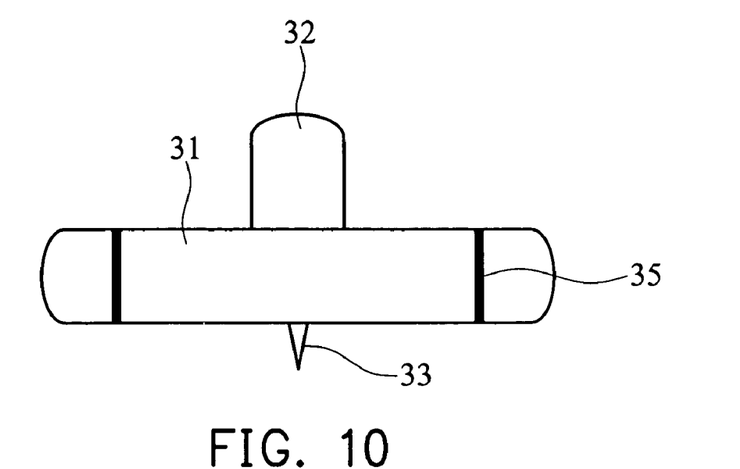
FIG. 10 is a front view of the flexible collecting bone dam.
Figure 11:
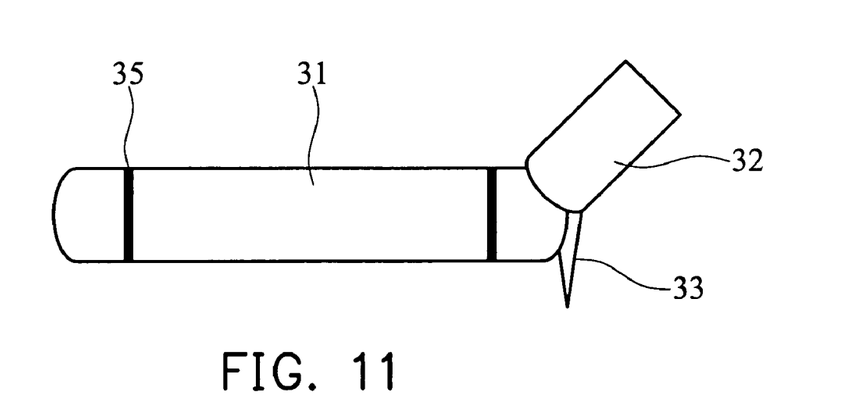
FIG. 11 is a side view of the flexible collecting bone dam.
Figure 12:
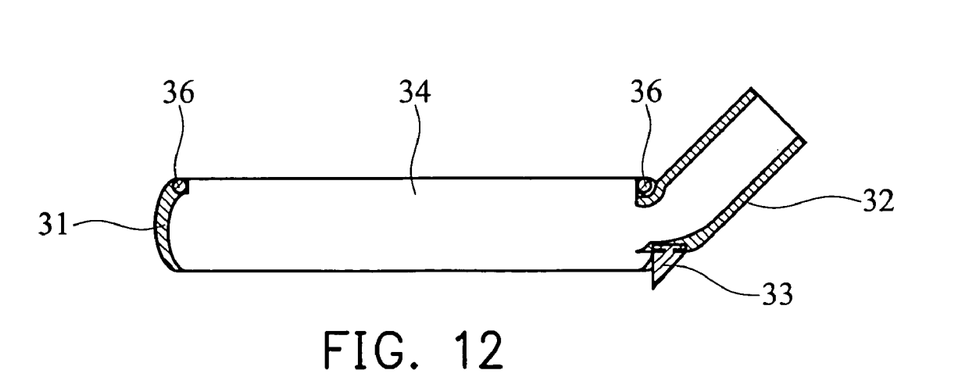
FIG. 12 is a cross section of the flexible collecting bone dam along a line A—A in FIG. 9.

Next, the operation of the device shown in the above is figures is described. A main unit body 1, including the filter member 4 as shown in FIG. 1, is disposed at a front end of a vacuum device, and collects bone pieces to be transplanted. After sufficient amount of bone pieces is collected, the main unit body 1 can be disassembled so as to remove the filter member 4. The outer surface of the filter member 4, including a filter part 13, is fitted into the inner surface of the filter holder 20, and is fixed at the filter holder 20 by press fitting an undercut of a first joint portion 17 of the filter member 4. By means of the above operation, since the filter member 4 is integrally formed with the filter holder 20, the filter member 4 can be stably positioned by the wider base diameter of a bottom part 22 of the filter holder 20. Furthermore, since an adhesive tape or a magic tape 21 is attached at the bottom part 22 of the filter holder 20, the filter holder 20 can be easily fixed to the operation cuff or the operating table. Thus, the filter member 4 can be prevented from being fallen down or being inclined, precious bone is collected without loss and can be removed easily. In addition, since the inner surface of the filter holder 20, including the filter member 4 with impermeability is fitted into the outer surface of the filter part 13, the bone pieces and the other substances can be held in the filter member 4 without leaking out through a mesh 15. Thus, in a case in which the bone is directly mixing agitated with the other substances for promoting bone construction of the transplant site, the collected bone pieces needs not to be transferred to other containers. Furthermore, since the inner or outer surface of the filter holder 20 is transparent or semi-transparent, the amount received therein can be easily weighed by a gradient. Thus, the amount of the bone pieces to be mixingly agitated with the other substances can be optimized. That is, it becomes possible to easily grasp in proportion the optimum amount of collected bone pieces with the other substances mixingly agitated with the bone pieces. Next, as shown in FIGS. 7–8, when collecting the self-bone from the oral cavity, the flexible bone collecting dam 30 shown in FIGS. 9–11 is assembled at the front end portion 5 via a second dam joint portion 32. A first dam joint portion 31 is positioned around a site to be excavated. The flexible bone collecting dam 30 can be fixed securely by a spike 33. The main unit body 1 is lifted upwardly in the direction shown by the arrow in FIG. 8. Since the bottom part of the first dam joint portion 31 corresponds to alveolar corrical bone 61, the bone can be prevented from loss by a storing space 34. At this time, mucoperiosteal flap 60 can be removed by the first jam joint portion 31 so as to be clearly seen. Thus, soft tissue can be prevented from damage by a cutting drill 51. A mark 35 on the flexible bone collecting dam 30 can correctly indicate the position of the bone to be cut. Furthermore, as shown in FIG. 12, a metallic annealing wire 36 can be previously inserted into the first dam joint portion 31. Thus, the bottom part of the first dam joint portion 31 can easily conform to any shape by pressing so as to correspond to the complex shape of the alveolar corrical bone 61.

Furthermore, the material and assembly manner of the second dam joint portion 32 are not limited, nor are the material and shape of the metallic annealing wire 36.

While the invention has been described by way of example and in terms of the preferred embodiment, it is to be understood that the invention is not limited to the disclosed embodiment. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A bone piece collecting device for filtering and collecting a bone piece from a liquid, comprising:
   a suction duct for collecting the liquid, comprising blood, saliva, cooling liquid including the bone piece from an oral cavity;
   a main unit body, including a suctioning side part and a base end side part, coaxialty connected to the suction duct via an intermediate portion, wherein the base end side part, through which the liquid excluding the bone piece passes, is detachable from the suction duct, and the suctioning side part, through which the liquid comprising at least the bone piece passes, is detachable from the base end side part;
   a filter member, including a filter part a first joint part and a second joint part and filtering the bone piece and jointing the base end side part and the suctioning side part, detachably disposed at the intermediate portion in the main unit body, wherein the filter part is container-shaped and filters the bone piece from the liquid, and the first joint part is fitted to an inner side of an opening of the base end side part, and the second joint part is fitted to an inner side of an opening of the suctioning side part and located around the first joint part and protrudes from the opening of the base end side part; and a filter holder including an inner wall, with impermeability, fitted to an outer wall of a mesh of the filter member removed from the main unit body after collecting the bone piece, wherein the area of a bottom part of the filter holder exceeds that of the filter member such that the filter member can be stably positioned, whereby a bone filling material comprising at least the bone piece can be collected from the filter member after the bone piece is mixing agitated with the other substances in the filter member.

2. The device as claimed in claim 1, further comprising an adhesive tape or a magic tape attached at the bottom part of the filter holder, such that the bone filling material can be collected from the filter member when the filter holder is fixed to an operation cuff or an operating table without manually holding.

3. The device as claimed in claim 1, wherein the filter holder is transparent or semi-transparent, and the filter holder includes a gradient thereon such that a volume received in the filter holder can be easily weighed.

4. The device as claimed in claim 1, wherein the main unit body further comprises a flexible bone collecting dam, and the flexible bone collecting dam comprises:

a first annular dam joint portion, including an opening at an inner side and surrounding a bone cutter, shaped as a hollow tube and made of flexible resin or formed with a metallic annealing wire previously inserted into the flexible resin so as to be deformable, whereby the first dam joint portion can be manually adapted to a site for operation;

a second dam joint portion, passing thorough an inner side of a hollow tube for jointing the suctioning side part of the main unit body at an outer side, being cylindrical; and a spike, disposed on a bottom part of the first dam joint portion, for fixing the flexible bone collecting dam to the site for operation, wherein the first dam joint portion is closely adjacent thereto, and is disposed around a site that the bone is cut, whereby the saliva can be prevented from sucking so that a maximum amount of collected bone can be collected without losing the collected bone and the amount collected cut bone can be increased.

5. The device as claimed in claim 1, wherein the filter holder is arranged apart from the main unit body, such that the filter member is moveable between a first position wherein the filter member is received in the main unit body and a second position wherein the filter member is removed from the main unit body and received in the filter holder.

* * * * *